United States Patent [19]

Zhu et al.

[11] Patent Number: 5,828,073
[45] Date of Patent: Oct. 27, 1998

[54] DUAL PURPOSE SHIELDED CONTAINER FOR A SYRINGE CONTAINING RADIOACTIVE MATERIAL

[75] Inventors: Bing Bing Zhu, Northridge; Monty Mong Chen Fu, Canyon Road; Richard L. Green, Simi Valley, all of Calif.

[73] Assignee: Syncor International Corporation, Woodland Hills, Calif.

[21] Appl. No.: 866,920

[22] Filed: May 30, 1997

[51] Int. Cl.$^6$ ........................................ G21F 5/00
[52] U.S. Cl. ..................... 250/506.1; 250/507.1
[58] Field of Search ............................ 250/506.1, 507.1, 250/515.1; 206/365, 364; 600/5

[56] References Cited

U.S. PATENT DOCUMENTS

| | | |
|---|---|---|
| D. 208,080 | 7/1967 | Hamilton . |
| D. 324,101 | 2/1992 | Reif et al. . |
| D. 333,347 | 2/1993 | Kemp et al. . |
| 2,682,352 | 6/1954 | Hawkins et al. . |
| 2,812,231 | 11/1957 | Zar . |
| 3,074,542 | 1/1963 | Myerson et al. . |
| 3,101,841 | 8/1963 | Baldwin . |
| 3,149,717 | 9/1964 | Castelli . |
| 3,272,322 | 9/1966 | Ogle . |
| 3,294,231 | 12/1966 | Vanderbeck . |
| 3,329,146 | 7/1967 | Waldman, Jr. . |
| 3,344,787 | 10/1967 | MacLean . |
| 3,367,488 | 2/1968 | Hamilton . |
| 3,531,644 | 9/1970 | Koster . |
| 3,673,411 | 6/1972 | Glasser . |
| 3,677,247 | 7/1972 | Brown . |
| 3,731,100 | 5/1973 | Lattin . |
| 3,882,315 | 5/1975 | Soldan . |
| 3,971,955 | 7/1976 | Heyer et al. . |
| 4,062,353 | 12/1977 | Foster et al. . |
| 4,081,688 | 3/1978 | Fries . |
| 4,092,546 | 5/1978 | Larrabee ............................ 250/506.1 |
| 4,106,622 | 8/1978 | Windischman . |
| 4,113,090 | 9/1978 | Carstens . |
| 4,122,836 | 10/1978 | Burnett . |
| 4,307,713 | 12/1981 | Galkin et al. . |
| 4,357,541 | 11/1982 | Ernst . |
| 4,382,512 | 5/1983 | Furminger . |
| 4,393,864 | 7/1983 | Galkin et al. . |
| 4,401,108 | 8/1983 | Galkin et al. . |
| 4,745,907 | 5/1988 | Russel, Jr. et al. . |
| 4,781,697 | 11/1988 | Slaughter . |
| 4,846,235 | 7/1989 | Handke . |
| 4,851,702 | 7/1989 | Perlman . |
| 4,869,299 | 9/1989 | Handke . |
| 4,892,525 | 1/1990 | Hermann, Jr. et al. . |
| 4,917,263 | 4/1990 | Korb . |
| 5,042,679 | 8/1991 | Crowson et al. . |
| 5,066,597 | 11/1991 | Stinson et al. . |
| 5,096,062 | 3/1992 | Burkardt et al. . |
| 5,099,998 | 3/1992 | Curzon et al. . |
| 5,145,063 | 9/1992 | Lee . |

(List continued on next page.)

OTHER PUBLICATIONS

Advertisement: May 1996, "The Solution To A Broken Syringe Is As Easy As 1–2–3," by Capintec, Inc.
Advertisement for "Syringe Shields" no date.
Advertisement for "Pro–Tec III® Syringe Shield" no date.
Advertisement for "Pro–Tec II® Syringe Shield" no date.
Advertisement for Pro–Tec β Syringe Shield. No date.
Advertisement for Pro–Tec® Syringe Shield. No date.
Syncor Corporation Brochure "Introducing the Secure™ Safety Injection Shield Another First!" No date.

*Primary Examiner*—Kiet T. Nguyen
*Attorney, Agent, or Firm*—Sheppard, Mullin, Richter & Hampton LLP; Keith A. Newburry, Esq.

[57] ABSTRACT

An improved radiopharmaceutical pig assembly and method for handling syringes containing radioactive material for use in the health care industry. The radiopharmaceutical pig assembly is preferably made of tungsten, is advantageously small, lightweight and has a dual function of also providing shielding for the syringe body during discharge of the syringe. An optional hand shield is also provided.

12 Claims, 4 Drawing Sheets

U.S. PATENT DOCUMENTS

| | | |
|---|---|---|
| 5,157,900 | 10/1992 | Kupersmit . |
| 5,205,408 | 4/1993 | Cobb . |
| 5,245,117 | 9/1993 | Withers et al. . |
| 5,274,239 | 12/1993 | Lane et al. . |
| 5,277,312 | 1/1994 | Vumbaca . |
| 5,303,836 | 4/1994 | Childress . |
| 5,323,719 | 6/1994 | Withers et al. . |
| 5,385,105 | 1/1995 | Withers, Jr. et al. . |
| 5,397,902 | 3/1995 | Castner et al. . |
| 5,417,326 | 5/1995 | Winer . |
| 5,519,931 | 5/1996 | Reich . |
| 5,536,945 | 7/1996 | Reich . |
| 5,552,612 | 9/1996 | Katayama et al. . |
| 5,672,883 | 9/1997 | Reich . |

FIG. 2
FIG. 3
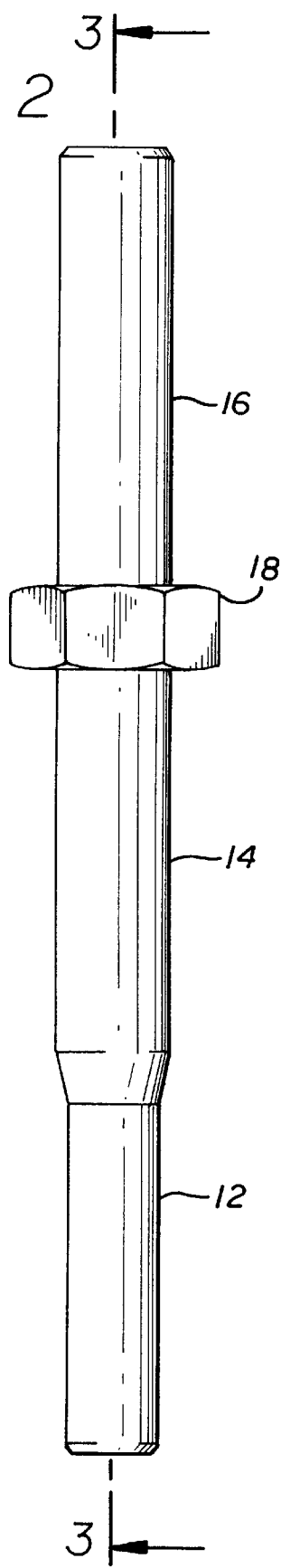
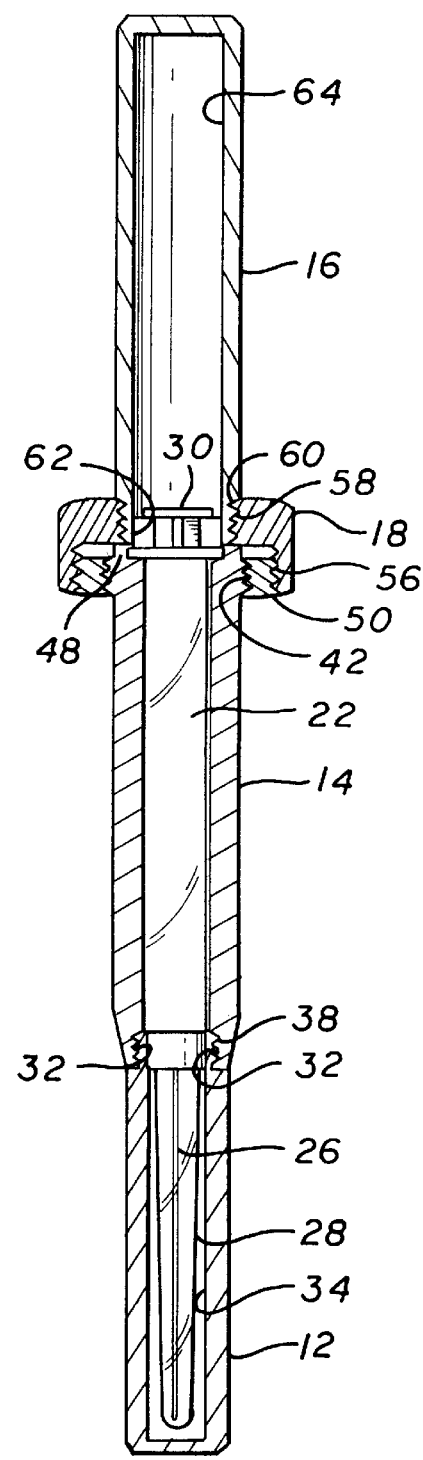

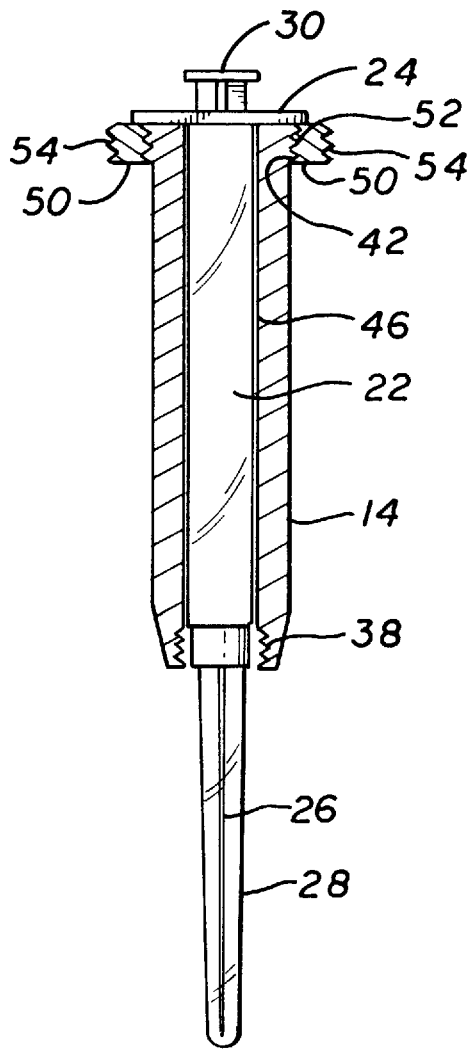
FIG. 4
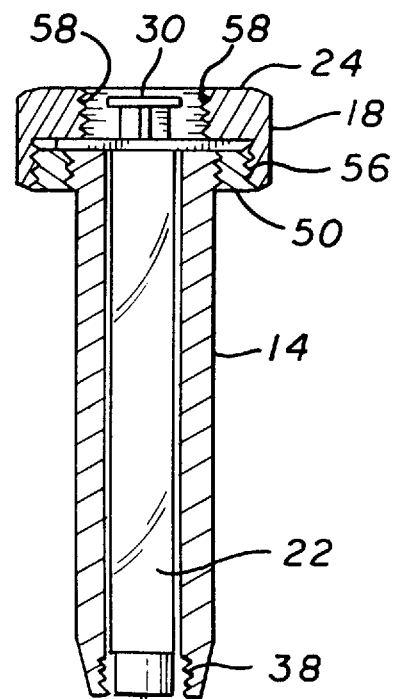
FIG. 5
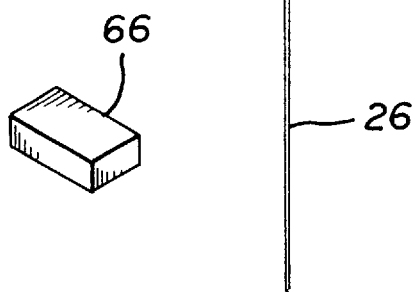

DUAL PURPOSE SHIELDED CONTAINER FOR A SYRINGE CONTAINING RADIOACTIVE MATERIAL

BACKGROUND OF THE INVENTION

The present invention generally relates to shielded containers for the handling of radioactive materials and, more particularly, to radiation-resistant, or radiation dense, shields allowing improved handling of radioactive materials used in the health care industry.

In the health care industry and more specifically in the field of nuclear medicine, radioactive materials known as radiopharmaceuticals are used in various applications, including non-invasive imaging of patients for various diagnostic, as well as therapeutic, purposes. Over the years, the health care industry has developed many different radiopharmaceuticals designed to facilitate such applications. Radiopharmaceuticals are generally used in a liquid form suitable for injection into a patient via standard 3 cc or 5 cc hypodermic syringes.

Because of the radioactive nature of radiopharmaceuticals, they should be handled carefully and various governmental agencies, including the U.S. Department of Transportation, the Nuclear Regulatory Commission, and the Occupational Health and Safety Administration, have promulgated regulations for safe handling of such materials. In addition to the radioactivity of the radiopharmaceutical, the biologically contaminated needle of the used syringe can pose a risk to disposal workers. To avoid some of the overhead costs associated with addressing the above concerns, many hospitals have resorted to outside pharmacy companies having expertise in the compounding and handling of radiopharmaceuticals.

Typically, health care providers order radiopharmaceuticals in syringes containing an individual dose for a specific patient. Methods and apparatus for the safe handling of syringes containing conventional radiopharmaceuticals have been developed. For example, a system for transporting syringes containing radiopharmaceuticals is disclosed in U.S. Pat. Nos. 5,519,931 and 5,536,945. The preferred embodiment of this system uses a radiopharmaceutical pig that has bulky and heavy lead shielding.

While this radiopharmaceutical pig has been generally satisfactorily, it has certain drawbacks. For example, the radiopharmaceutical pig is heavy and its weight limits the number of radiopharmaceutical pigs that can be carried by a health care worker. Further, the physical size of the radiopharmaceutical pig is such that it cannot be conveniently carried in the pocket of a medical coat. Another drawback is related to the handling of the syringe within the pig after it has been transported from the pharmacy to the hospital. In particular, a hospital worker must open the radiopharmaceutical pig, remove the syringe, and place it in a special syringe shield that allows the worker to discharge the syringe. To enable the worker to discharge the syringe, this syringe shield encloses the body of the syringe, but not the syringe plunger and needle. During the transfer of the syringe from the radiopharmaceutical pig to the syringe shield, the entire syringe is exposed and there is a period of radiation exposure because the syringe is not shielded.

Accordingly, there exists a need for a compact, lightweight radiopharmaceutical pig that can be readily converted from a container used to deliver a syringe containing radioactive material to a syringe shield for the discharge of the syringe. The present invention satisfies this need and provides further related advantages.

SUMMARY OF THE INVENTION

Briefly, and in general terms, the present invention resides in an improved radiopharmaceutical pig assembly for handling syringes containing radioactive material for use in the health care industry. As will be described below, the radiopharmaceutical pig assembly is advantageously small, lightweight and has a dual function of also providing shielding for the syringe body during discharge of the syringe.

More specifically, and by way of example only, the radiopharmaceutical pig assembly is for shielding a syringe containing radioactive material during transport and discharge of the syringe. The syringe has a flanged body with a needle and an opposing plunger extending therefrom. The radiopharmaceutical pig assembly includes a radiation-dense lower, mid and upper body portions. The lower body portion has a threaded upper end and an interior surface defining a first internal cavity with an opening in the upper end sized to accept the needle of the syringe therein. The radiation-dense mid body portion has a upper end, a lower end and an interior surface extending therebetween to define a passageway between the openings. The passage is sized to accept the body of the syringe therein and the lower end of the mid body portion is threaded to releasably engage the threads on the lower body portion.

The passage in the mid body portion is located in alignment with the cavity in the lower body portion and a locknut threadedly engages the upper end of the lower body portion. The radiation-dense upper body portion has a lower end and an interior surface defining a second internal cavity with an opening in the lower end of the upper body portion. The opening and cavity are sized to accept the plunger of the syringe therein and the lower end is threaded to releasably engage the locknut so that the passageway in the mid body portion is located in alignment with the cavity in the upper body portion. The locknut advantageously fastens the syringe in the mid body portion of the assembly.

The body portions of the radiopharmaceutical pig assembly are preferably made of tungsten, a metal having superior radiation shielding properties as compared to lead, which has long been used for the shielding of radiopharmaceuticals. Thus, a much smaller radiopharmaceutical pig assembly is believed to shield as well or better than a large and heavy conventional lead radiopharmaceutical pig. This size and weight reduction enables easy handling by health care workers, thereby reducing labor costs and the time needed for the handling of a radiopharmaceutical. For example, because the radiopharmaceutical pig assembly is much lighter than a conventional lead pig, health care workers can more easily move the pig and can even place it in a pocket of their lab coat without discomfort due to its weight. Further, because the radiopharmaceutical pig assembly is about 50% lighter and is much smaller than a lead pig, a health care worker can now move more radiopharmaceutical pigs than previously possible, resulting in cost savings.

In another embodiment of the invention, a hand shield is provided that is releasably engageable with the mid body portion to protect the hand of a health care worker when the needle of the syringe is exposed. In another embodiment of the invention, a method of transporting and discharging a syringe containing radioactive material is provided, using the dual purpose radiopharmaceutical pig assembly and, in a more detailed embodiment, a needle incinerator that advantageously and quickly removes the contaminated syringe needle and seals the needle end of the syringe. In yet another embodiment of the invention, a lens is mounted in the mid body portion to magnify the body of the syringe.

Other features and advantages of the present invention will become apparent from the following description of the preferred embodiment, taken in conjunction with the accompanying drawings, which illustrate, by way of example, the principles of the invention.

BRIEF DESCRIPTION OF THE DRAWINGS

The following drawings illustrate a presently preferred embodiment of the invention, in which:

FIG. 2 is a side view of the radiopharmaceutical pig assembly of FIG. 1;

FIG. 3 is a cross sectional view of the radiopharmaceutical pig assembly of FIG. 2, taken along lines 3—3;

FIG. 4 is a cross sectional view of the middle portion of the radiopharmaceutical pig assembly of FIG. 3, shown holding the syringe;

FIG. 5 is a cross sectional view of the middle portion of the radiopharmaceutical pig assembly of FIG. 3, shown with a locknut holding the syringe thereon.

DESCRIPTION OF THE PREFERRED EMBODIMENT

Figure 1:
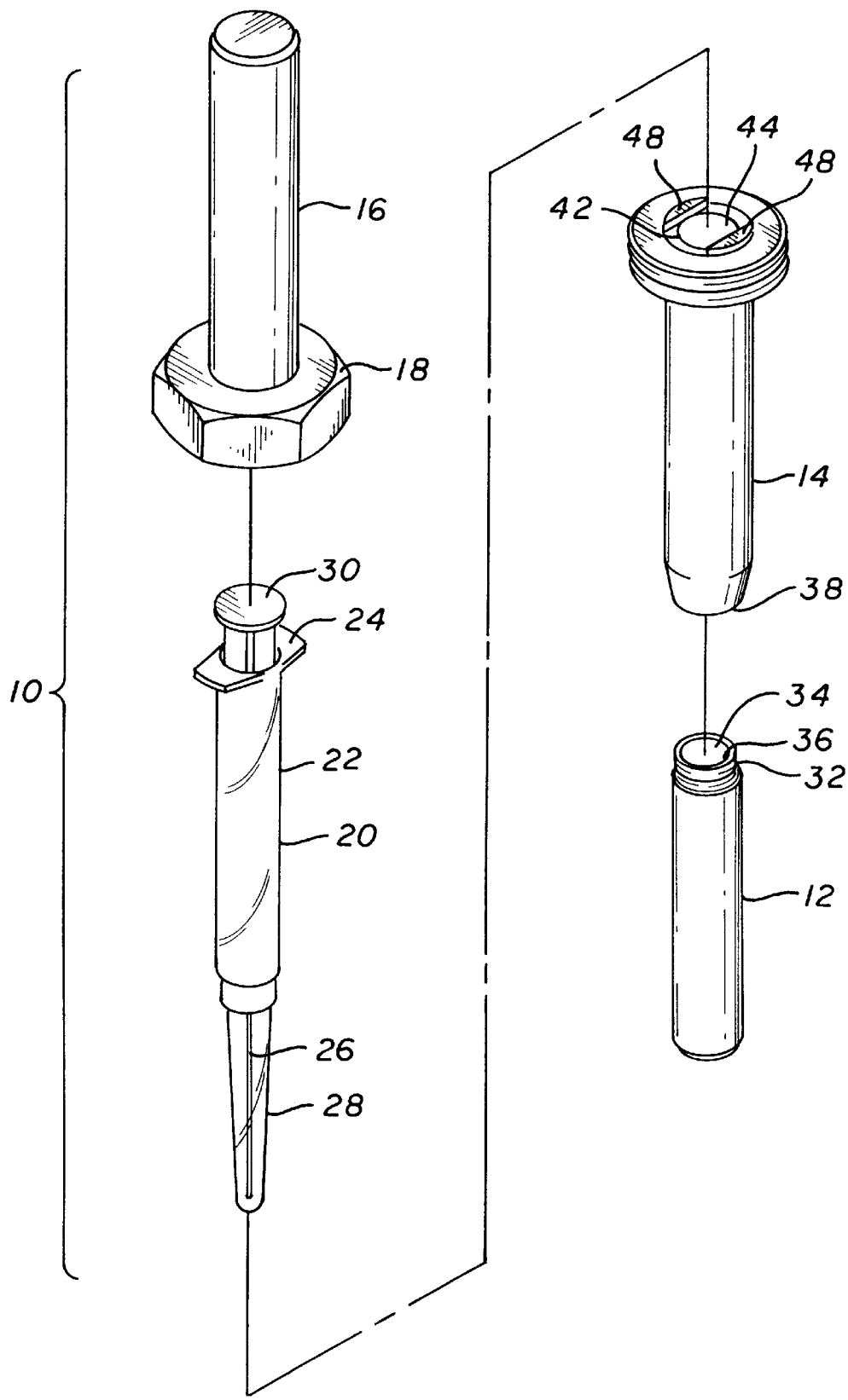
FIG. 1 is an exploded perspective view of a preferred embodiment of a radiopharmaceutical pig assembly for holding a syringe containing radioactive material.

Referring now to the drawings, and particularly to FIGS. 1–5 thereof, one embodiment of the invention is a dual purpose radiopharmaceutical pig assembly to transport and discharge a syringe containing a radioactive material. The radiopharmaceutical pig assembly is generally referred to by the reference numeral 10 and includes a lower body portion 12, a mid body portion 14, an upper body portion 16, and a locknut 18. The syringe 20 can be a standard 3 cc. or 5 cc. type that has a tubular body 22 with a flanged end 24, a needle 26, a needle cap 28 and a plunger 30.

The body portions 12–16 of the radiopharmaceutical pig assembly 10 are preferably made of tungsten, a metal having superior radiation shielding properties as compared to lead, which has long been used for the shielding of radiopharmaceuticals. The wall thickness of the body portions can vary from 0.3 inch in the mid body portion 14 to 0.175 inch in the upper or lower body portions 12 and 16. A radiopharmaceutical pig assembly with the aforementioned dimensions is believed to shield as well or better than a large and heavy conventional lead radiopharmaceutical pig. Due to its superior shielding properties, the radiopharmaceutical pig assembly is smaller and much lighter than would otherwise be possible if it was made from lead. This size and weight reduction enables easy handling by health care workers, thereby reducing labor costs and the time needed for the handling of a radiopharmaceutical. For example, because the radiopharmaceutical pig assembly is much lighter than a conventional lead pig, health care workers can more easily move the pig and can even place it in a pocket of their lab coat without discomfort due to its weight. Further, because the radiopharmaceutical pig assembly is about 50% lighter and is much smaller than a lead pig, a health care worker can now move more radiopharmaceutical pigs than previously possible, resulting in cost savings.

The lower body portion 12 has a threaded upper end 32 and an interior cavity 34 extending downward from an opening 36 therein. The cavity is sized to accept the capped end 28 of the syringe 20 therein. The threaded upper end of the lower body portion engages a threaded lower end 38 of the mid body portion 14. The mid body portion includes an opening 40 in its lower end and also includes a threaded upper end 42 with an opening therein 44, and an interior passage 46 therebetween the openings 40 and 44. The passage 46 is aligned with the cavity 34 in the lower body portion 12 and is sized to accept the body of the syringe 22 therein.

The upper end 42 of the mid body section also includes two raised opposing walls 48 and a ring 50 with threads on its outside and inside edges 52 and 54. The ring engages the threaded upper end 24 of the mid body portion and threads 56 on the locknut 18. The locknut has another set of threads 58 to releasably engage a threaded lower end 60 of the upper body portion 16. The upper body portion 16 has an opening 62 and an internal cavity 64 sized to accept the plunger 30 of the syringe 22 therein.

One advantage of this three-piece radiopharmaceutical pig assembly 10 is illustrated in FIGS. 4–5. The syringe 20 can be discharged into the patient without removing the syringe from the mid body portion 14. Thus, the mid body portion 14 of the radiopharmaceutical pig assembly 10 advantageously shields workers from the body of the syringe 22 after the radiopharmaceutical pig 10 is received in the area of the patient to be treated and during the discharge of the syringe. A health care worker can remove the upper and lower body portions 12 and 16 from the mid body portion 14 to expose the needle 26 and plunger 30 of the syringe. The needle can then be positioned for injection and the plunger can be depressed without removing the syringe from the beneficial shielding provided by the mid body piece. Another advantage is related to the locknut 18, which abuts the flange of the syringe 24 to hold the syringe down when upward pressure is applied from inserting the needle into a patient or an intravenous port.

Another advantage is provided when the radiopharmaceutical pig assembly is used in conjunction with a commonly available needle incinerator 66. After discharge, the contaminated needle 26 of the syringe can be incinerated, causing the plastic body of the syringe to melt and become sealed where the needle once was located. Accordingly, it can be appreciated that the risk of needle stick to disposal workers and the risk of leaking of the radioactive material remaining in the syringe 20 is advantageously reduced.

Figure 6:
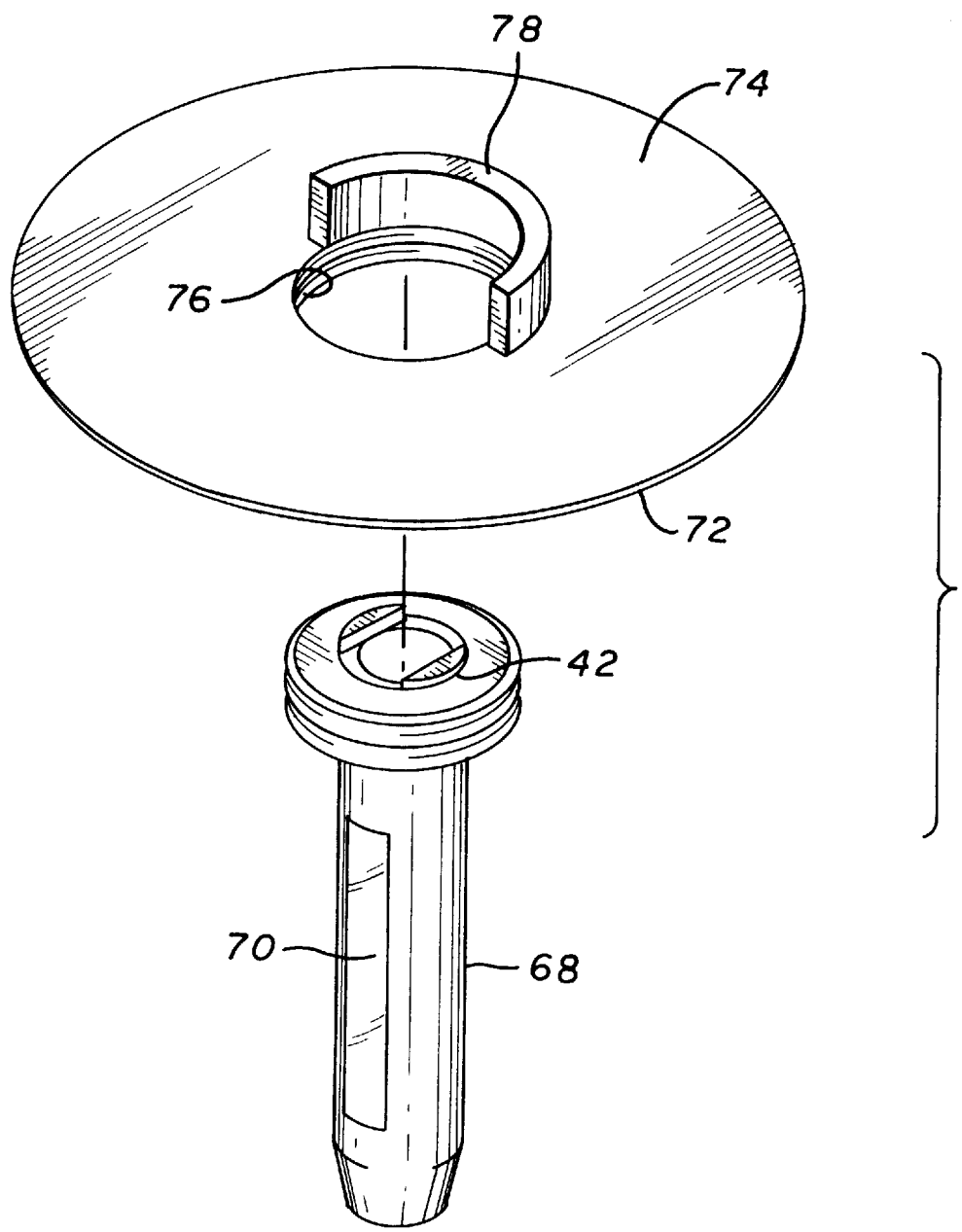
FIG. 6 is a perspective view of a second embodiment of a mid body portion of the radiopharmaceutical pig assembly, shown with an optional hand shield.

FIG. 6 shows a alternative embodiment of a mid body portion 68 that includes a window, or lens, 70 for the magnification of the syringe body 22. An optional hand shield 72 can also be attached to the upper end 42 of either version of the mid body portion 68 or 14. The shield has a disk-shaped plate 74 with a threaded central hole 76 and a raised semi-circular wall 78 that is grippable by the hand of a health care worker. This shield can protect the worker's hand and lower arm from needle stick.

While a particular form of the invention has been illustrated and described, it will be apparent that various modifications can be made without departing from the spirit and scope of the invention. Accordingly, it is not intended that the invention be limited, except as by the claims to be filed in this matter.

We claim:

1. A radiopharmaceutical pig assembly for shielding a syringe containing radioactive material during transport and discharge of the syringe, the syringe having a flanged body with a needle and an opposing plunger extending therefrom, the radiopharmaceutical pig assembly comprising:

a radiation-dense lower body portion having a threaded upper end, and an interior surface defining a first internal cavity with an opening in the upper end sized to accept the needle of the syringe therein;

a radiation-dense mid body portion having a upper end, a lower end and an interior surface extending therebetween to define a passageway between openings in the upper and lower ends of the mid body portion, the passage sized to accept the body of the syringe therein, the lower end of the mid body portion being threaded to releasably engage the threads on the lower body portion, the passage in the mid body portion located in alignment with the cavity in the lower body portion upon their engagement;

a locknut threadedly engaging the upper end of the mid body portion; and a radiation-dense upper body portion having a lower end and an interior surface defining a second internal cavity with an opening in the lower end of the upper body portion, the opening and cavity being sized to accept the plunger of the syringe therein, the lower end being threaded to releasably engage the locknut such that the passageway in the mid body portion is located in alignment with the cavity in the upper body portion.

2. The radiopharmaceutical pig assembly as defined in claim 1, wherein the passage in the mid body portion is sized such that the flanged end of the syringe abuts the upper end of the mid body portion to prevent the syringe from falling through the mid body portion.

3. The radiopharmaceutical pig assembly as defined in claim 1, wherein the lower body portion, the mid body portion and the upper body portion are made of tungsten.

4. The radiopharmaceutical pig assembly as defined in claim 3, wherein the lower body portion, the mid body portion and the upper body portion are made of tungsten that is less than 0.3 inch thick.

5. The radiopharmaceutical pig assembly as defined in claim 1, wherein the lower body portion, the mid body portion and the upper body portion have walls that are less than 0.3 inch thick.

6. The radiopharmaceutical pig assembly as defined in claim 1, wherein the upper end of the mid body portion has opposing walls to engage the flange of the syringe and prevent rotation thereof.

7. The radiopharmaceutical pig assembly as defined in claim 1, further comprising a hand shield releasably engageable with one end of the mid body portion.

8. The radiopharmaceutical pig assembly as defined in claim 1, further comprising a lens placed in an opening in the midbody portion, the lens magnifying the body of the syringe.

9. A radiopharmaceutical pig assembly for enclosing a syringe containing radioactive material during transport and discharge of the syringe, the syringe having a flanged body with a needle and an opposing plunger extending therefrom, the radiopharmaceutical pig assembly comprising:

a tungsten lower body portion having an upper end and an interior surface defining a first internal cavity with an opening in the upper end sized to accept the needle of the syringe therein;

a tungsten mid body portion having an upper end, a lower end and an interior surface extending therebetween to define a passageway between openings in the upper and lower ends of the mid body portion, the passage sized to accept the body of the syringe therein, the lower end of the mid body portion releasably engageable with the upper end of the lower body portion to locate the passage in the mid body portion in alignment with the cavity in the lower body portion; and a tungsten upper body portion having a lower end and an interior surface defining a second internal cavity with an opening in the lower end of the upper body portion, the opening and cavity being sized to accept the plunger of the syringe therein, the lower end of the upper body portion releasably mountable to the upper end of the mid body portion such that the passageway in the mid body portion is located in alignment with the cavity in the upper body portion, wherein the interior surfaces of all the body portions cooperatively enclose the syringe.

10. The radiopharmaceutical pig assembly as defined in claim 9, wherein the lower body portion, the mid body portion and the upper body portion are made of tungsten that is less than 0.3 inch thick.

11. A method of transporting and discharging a syringe containing radioactive material utilizing a dual purpose radiopharmaceutical pig having removable upper and lower body portions, the syringe having a body with a needle and an opposing plunger extending from the body, the method comprising:

receiving the radiopharmaceutical pig holding the syringe containing the radioactive material;

removing the upper and lower body portions of the radiopharmaceutical pig to expose the needle and the plunger of the syringe and retain a portion of the radiopharmaceutical pig to shield the body of the syringe;

positioning the remaining portion of the radiopharmaceutical pig containing the syringe such that the needle of the syringe is in a predetermined location for discharge; and pushing the plunger of the syringe downward to force radioactive material out of the syringe.

12. The method as defined in claim 11, further comprising incinerating the needle of the syringe after the discharge of the syringe to seal the syringe for disposal purposes.

* * * * *